(12) United States Patent
Chan et al.

(10) Patent No.: US 6,383,788 B1
(45) Date of Patent: *May 7, 2002

(54) MINIMIZING THERMALLY INDUCED AGGREGATION OF DNASE IN SOLUTION WITH CALCIUM

(75) Inventors: Hak-Kim Chan, North Sydney (AU); Igor Gonda, San Francisco, CA (US); Steven J. Shire, Belmont, CA (US); Suzanne Sin-Mui Lo Weck, Mountain View, CA (US)

(73) Assignee: Genentech, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/696,955

(22) PCT Filed: Feb. 28, 1995

(86) PCT No.: PCT/US95/02457

§ 371 Date: Dec. 3, 1996

§ 102(e) Date: Dec. 3, 1996

(87) PCT Pub. No.: WO95/23854

PCT Pub. Date: Sep. 8, 1995

Related U.S. Application Data (63) Continuation-in-part of application No. 08/377,527, filed on Jan. 20, 1995, now abandoned, which is a continuation of application No. 08/206,504, filed on Mar. 4, 1994, now abandoned.

(51) Int. Cl.$^7$ .............................. C12N 9/96; C12N 9/16
(52) U.S. Cl. ....................................... 435/188; 435/196
(58) Field of Search .................................. 435/188, 196

(56) References Cited

U.S. PATENT DOCUMENTS

| | | | | |
|---|---|---|---|---|
| 3,042,587 A | * | 7/1962 | Baumgarten et al. | 435/188 |
| 4,065,355 A | | 12/1977 | Khouw et al. | 435/199 |
| 4,233,405 A | * | 11/1980 | Neubeck | 435/187 |
| 5,279,823 A | * | 1/1994 | Frenz et al. | 424/94.61 |

FOREIGN PATENT DOCUMENTS

| | | |
|---|---|---|
| WO | 90/07572 | 7/1990 |
| WO | 93/25670 | 12/1993 |

OTHER PUBLICATIONS

Tullis et al., "The Effect of Calcium and Magnesium on the Ultraviolet Spectrum of Bovine Pancreatic Deoxyribonuclease A" (1974) J. Biol. Chem., 249(16), pp. 5033–5037.*
Douvas et al., "Some Effects of Calcium and Magnesium Ions on the Activity of Bovine Pancreatic Deoxyribonuclease A" (1975) Biochim. Biophys. Acta, 395(2), pp. 201–212.*
Price, P.A., "The Essential Role of Ca2+ in the Activity of Bovine Pancreatic Deoxyribonuclease" (1975) J. Biol. Chem., 250(6), pp. 1981–1986.*
Lizarraga et al., "The Role of Ca2+ on pH–Induced Hydrodynamic Changes of Bovine Pancreatic Deoxyribonuclease A" (1978) J. Biol. Chem., 253(9), pp. 3191–3195.*
Lizarraga et al., "Multiple Conformations of Deoxyribonuclease A, Their Separation at Alkaline pH and Low Ionic Strength in the Presence of Ca2+" (1979) Biochim. Biophys. Acta, 579(2), pp. 298–302.*
Schellman, J.A., Ann. Rev. Biophys. Biophys. Chem. Rev., 16, "The Thermodynamic Stability of Proteins", pp. 115–137, 1987.*
Liao, Ta–Hsiu, et al., "Bovine Pancreatic Deoxyribonuclease A, Isolation of Cyanogen Bromide Peptides; Complete Covalent Structure of the Polypeptide Chain," *The Journal of Biological Chemistry*, 248(4):1489–1495 (1973).
Lourenco, R.V., et al., "Clinical Aerosols, II. Therapeutic Aerosols," *Arch. Intern. Med.*, 142:2299–2308 (1982).
Shak, S., et al., "Recombinant Human DNASE I Reduces the Viscosity of Cystic Fibrosis Sputum," *Proc. Natl. Acad. Sci. USA*, 98:9188–9192 (1990).
Hubbard, R.C., et al., "A Preliminary Study of Aerosolized Recombinant Human Deoxyribonuclease I in the Treatment of Cystic Fibrosis," *The New England Journal of Medicine*, 326(12):812–815 (1992).
Markey, F., "Rapid Purification of Deoxyribonuclease I Using Fast Protein Liquid Chromatography," *Elsevier Science Publishes V.V., Federation of European Biochemical Societies*, 167(1):155–159 (1989).
Nefsky, B., et al., "Preparation of Immmobilized Monomeric Actin and its Use in the Isolation of Protease–Free and Ribonuclease–free Pancreatic Deoxyribonuclease I," *Eur. J. Biochem.*, 179:215–219 (1989).
Bell, J.H., et al., "Dry Powder Aerosols I: A New Powder Inhalation Device," *Journal of Pharmaceutical Sciences*, 60(10):1559–1564 (1971).
Vidgren, M., et al., "Effect of Powder Inhaler Design on Drug Deposition in the Respiratory Tract," *International Journal of Pharmaceutics*, 42:211–216 (1988).

(List continued on next page.)

Primary Examiner—Jon P. Weber
(74) Attorney, Agent, or Firm—Flehr Hohbach Test Albritton & Herbert LLP (57) ABSTRACT

The present invention relates to the use of calcium ion and/or sugars to minimize thermal aggregation of DNase and to the use of calcium ion to stabilize liquid solutions of DNase, the solutions having a pH of less than neutral. DNase is the active pharmaceutical principle and the solutions may contain other pharmaceutically acceptable excipients making them suitable for pharmaceutical administration. In the first instance, calcium ion/sugar minimizes the effects of thermal aggregation in the solution. In the second aspect, calcium ion stabilizes the lower pH solutions from protein precipitation.

6 Claims, 8 Drawing Sheets

OTHER PUBLICATIONS

Kassem, N.M., et al., "The Effect of Air Flow and Carrier Size on the Characteristics of an Inspirable Cloud," *Chelsea Department of Pharmacy, King's College, London SW3 6LX* 14P in Auty, R., et al. *Br. J. Dis. Ches.*, 81:371–380 (1987); and in Richards, R., et al., *Eur. Respir. J.*, 1:896–901 (1988).

Kassem, N.M., et al., "The Influence of Carrier Surface on the Characteristics of Inspirable Powder Aerosols," *Chelsea Department of Pharmacy, King's College, London SW3 6LX*, 11P in Staniforth, J., et al., *J. Pharm. Pharmacol.*, 34:141–145 (1982); and in Kassem, N.M., et al., *J. Pharm. Pharmacol.*, 41(Supp.):13P (1989).

Mumenthaler, M., et al., "Feasibility Study on Spray–Drying Protein Pharmaceuticals: Recombinant Human Growth Hormone and Tissue–Type Plasminogen Activator," *Pharmaceutical Research*, 11(1):12–20 (1994).

Granderton, D., "The Generation of Respirable Clouds Form Coarse Powder Aggregates," *Journal of Biopharmaceutical Sciences*, 3(1/2):101–105 (1992).

Franks, F., et al., "Materials Science and the Production of Shelf–Stable Biologicals," *BioPharm*, pp. 38–42 & 55 (1991).

van der Beek, M.J., et al., "Preservation of the Enzymatic Activity of Rennin During Spray Drying and During Storage, and the Effect of Sugars and Certain Other Additives," *Neth. Milk Dairy J.*, 23:46–54 (1969).

Schmid, R.D., "Stabilised Soluble Enzymes," *Advances in Biochemical Engineering*, 12:42–118 (1979).

Arakawa, T., et al., "Stabilization of Protein Structure by Sugars," *Biochemistry*, 21:6436–6544 (1982).

Back, J.F., et al., "Increased Thermal Stability of Proteins in the Presence of Sugars and Polyols," *Biochemistry*, 18(23):5191–5196 (1979).*

Gekko, K., "Calorimetric Study on Thermal Denaturation of Lysozyme in Polyol–Water Mixtures," *J. Biochem*, 91:1197–1204 (1982).*

Cipolla, D.C., et al., "Assessment of Aerosol Delivery Systems for Recombinant Human Deoxyribonuclease," *S.T.P. Pharma Sciences*, 4(1):50–62 (1994).*

Cipolla, D., et al., "Characterization of Aerosols of Human Recombinant Deoxyribonuclease I (rhDNase) Generated by Jet Nebulizers," *Pharmaceutical Research*, 11(4):491–498 (1994).*

Kim, C.S., et al., "Particle Deposition in Bifurcating Airway Models with Varying Airway Geometry," *J. Aerosol Sci.*, 25(3):567–581 (1994).*

Lundblad et al. (1977) J. Dent. Res., 56(3), "Purification and Partial Characterization of Deoxyribonuclease I from Bovine Parotid Gland", pp. 320–326.*

Broadhead et al. (1992) Drug Dev. Indust. Pharm., 18(11&12). "The Spray Drying of Pharmaceuticals", pp. 1169–1206.*

Price et al. (1969a) J. Biol. Chem., 244(4), "Properties of Chromatographically Purified Bovine Pancreatic Deoxyribonuclease", pp. 917–923.*

Price et al. (1969b) J. Biol. Chem., 244(4), "Alkylation of a Histidine Residue at the Active Site of Bovine Pancreatic Deoxyribonuclease", pp. 924–928.*

Price et al. (1969c) J. Biol. Chem., 244(4), "Effect of Divalent Cations on the Reduction and Re–Formation of the Disulfide Bonds of Deoxyribonuclease", pp. 929–932.*

Eichhorn et al. (1969) J. Biol. Chem., 244(4), "The Interaction of Metal Ions with Polynucleotides and Related Compounds", pp. 937–942.*

Sigma Molecular Biology Catalog (1993) p. 38.*

* cited by examiner

MINIMIZING THERMALLY INDUCED AGGREGATION OF DNASE IN SOLUTION WITH CALCIUM

CROSS-REFERENCE TO RELATED APPLICATIONS

The present application is a continuation-in-part of U.S. Ser. No. 08/377,527, filed Jan. 20, 1995, now abandoned, which is a continuation of U.S. Ser. No. 08/206,504 filed Mar. 4, 1994, now abandoned. The present application is related in subject matter to the disclosure contained in U.S. patent application Ser. No. 07/448,038, filed Dec. 8, 1989, now abandoned, and in U.S. patent application Ser. No. 07/289,958, filed Dec. 23, 1988, now abandoned, and in U.S. patent application Ser. No. 07/895,300, filed Jun. 8, 1992, now U.S. Pat. No. 5,279,823, and in U.S. patent application Ser. No. 08/206,020, filed on Mar. 4, 1994, now abandoned. The content of these prior applications is hereby expressly incorporated by reference herein.

FIELD OF THE INVENTION

The present invention is related to results obtained from research on the formulation of deoxyribonuclease, otherwise referred to as DNase, a phosphodiesterase that is capable of hydrolyzing polydeoxyribonucleic acid (DNA).

The present invention relates generally to the preparation of liquid solutions of DNase that are protected from thermally induced aggregation of the DNase active principal component. The present invention relates additionally generally to the preparation of liquid solutions of DNase that are maintained stable at pHs of less than neutral.

It relates to these solutions per se and to their methods of preparation and to their use clinically or for preparing further formulations useful clinically in the treatment of disorders susceptible to the biological activity of DNase, as discussed in more detail infra.

BACKGROUND OF THE INVENTION

DNase is a phosphodiesterase capable of hydrolyzing polydeoxyribonucleic acid. DNase has been purified from various species to various degrees. The complete amino acid sequence for a mammalian DNase was first made available in 1973. See, e.g., Liao, et al., *J. Biol. Chem.* 248, 1489 (1973).

DNase has a number of known utilities and has been used for therapeutic purposes. Its principal therapeutic use has been to reduce the viscoelasticity of pulmonary secretions in such diseases as pneumonia and cystic fibrosis, thereby aiding in the clearing of respiratory airways. See, e.g., Lourenco, et al., *Arch. Intern. Med.* 142, 2299 (1982); Shak, et al., *Proc. Nat. Acad. Sci.* 87, 9188 (1990); and Hubbard, et al., *New England Journal of Medicine* 326, 812 (1992).

DNA encoding human DNase has been isolated and sequenced and that DNA has been expressed in recombinant mammalian host cells, thereby enabling the production of human DNase in mammalian commercially useful quantities. See, e.g., Shak, et al., *Proc. Nat. Acad. Sci.* 87, 9188 (1990). Recombinant human DNase (rhDNase) has been found to be useful clinically, especially in purified form such that the DNase is free from proteases and other proteins with which it is ordinarily associated in nature.

The means and methods by which human DNase can be obtained in pharmaceutically effective form is described in the patent applications cited above. Various specific methods for the purification of DNase are known in the art. See, e.g., Khouw, et al., U.S. Pat. No. 4,065,355, issued Dec. 27, 1977; Markey, *FEBS Letters* 167, 155 (1984); and Nefsky, et al., *Euro. Journ. Biochem.* 179, 215 (1989).

The present application is predicated on the use of such DNase for formulation. DNase can be employed as such, as a mixture of deamidated and non-deamidated forms, or in isolated deamidated and non-deamidated forms. The preparation and separation of such forms are the subject matter of a patent application cited above.

The present invention is directed to the preparation of liquid solutions of DNase (including all of its biologically active forms as previously noted) that are stable to thermally induced aggregation of DNase.

The present invention is directed to the preparation of stabilized liquid solutions of DNase (including all of its biologically active forms as previously noted). These liquid solutions containing DNase in substantially non-deamidated form are maintained at pHs of less than neutral in stable form such that precipitation of material does not occur to any substantial extent, and therefore, the solutions are in a clear form suitable for pharmaceutical administration. Such less than neutral pH levels result in a reduction of the rate of deamidation of the DNase principle during storage. At storage at elevated temperatures (upwards of 37° C.), such lower pH solutions result in precipitation products. The present invention, in an aspect, stabilizes such solutions from such precipitation.

SUMMARY OF THE INVENTION

The present invention is predicated upon the finding of an exceptional characteristic found attributable to a particular component which in liquid solution together with DNase as biologically active principle, protects said DNase from thermally induced aggregation. This particular component in liquid solution together with DNase as biologically active principle protects and stabilizes the solution from precipitation effects resulting in clear solutions which are suitable for pharmaceutical administration.

The pharmaceutical specifications permitting the storage with suitable shelf life of DNase requires the retention of at least 80% biological potency at from 2 to 8° C. over a sustained period of time. The recommended pH of such solutions are about neutral, more particularly approximately 6.5. It has been discovered that at this pH range, deamidation occurs at a relatively constant rate resulting in solutions in which the DNase component is increasingly deamidated. The deamidation takes place at the asparagine residue that occurs at position 74 in the amino acid sequence of native mature DNase. Attention is directed to U.S. Ser. No. 07/895,300, filed Jun. 8, 1992. In that application attention is focused on the separation of deamidated and non-deamidated DNase from one another for separate formulation into pharmaceutically administrable forms.

In this aspect of the present invention, it has been found that lowering the pH of such liquid solutions containing DNase substantially reduces the rate constant of deamidation resulting in liquid formulations which are relatively stable as to deamidation and thus the DNase remains in its non-deamidated form which is biologically more potent. However, the reduction of pH results in a by-process of precipitation of materials from the liquid solutions when stored at about 37° C., which is unacceptable from a pharmaceutical formulation standpoint.

The present invention in this aspect relates to the stabilization of such less than neutral pH liquid solutions containing DNase from precipitation resulting in solutions that are pharmaceutically administrable.

The introduction and use of calcium ion ($Ca^{+2}$) protects such less than neutral pH liquid solutions of DNase from precipitation resulting in clear solutions that are suitable for pharmaceutical storage and administration, without the need for refrigeration. Thus, the present invention in this aspect relates to a method of stabilizing liquid solutions containing DNase as active principle, such solutions being at a pH of less than neutral such that deamidation is deterred or inhibited which comprises employing amounts of calcium ion in said solution that protect such solutions from precipitation resulting in liquid formulations of DNase that are suitable for storage and ultimate pharmaceutical administration. These solutions are maintained in a stable form without any or any substantial precipitation that otherwise occurs at pHs of less than neutral. Further, these solutions result in a minimal deamidation of the active component of DNase.

In the alternative aspect of the present invention, in signal distinction from certain other divalent cations, calcium ion ($Ca^{+2}$) additionally protects DNase from thermally induced aggregation in liquid solution. Thus, the present invention relates to a process of minimizing thermally induced aggregation of DNase in liquid solution comprising DNase as active principle which comprises employing DNase-aggregation-minimizing amounts of calcium ion in said solution.

In a further embodiment of this alternative aspect of this invention, protection of DNase from thermally induced aggregation in liquid solution is obtained by the addition of sugars to said solutions, either in lieu of or additional to the presence of calcium ion.

Thus, the present invention is directed to methods for the preparation of liquid solutions comprising DNase as active principle which comprising using in said solutions an amount of calcium ion and/or sugar that: 1) minimizes DNase aggregation brought about from thermal instability (a DNase-aggregation-minimizing amount) and an amount of calcium ion that 2) stabilizes said solutions that are at a pH of less than neutral from precipitation resulting in said solutions being clear and thus in a form suitable for storage and pharmaceutical administration. In the latter, deamidation of the DNase is inhibited, a consequence of the lowered pH (from neutral).

Stated another way, the present invention is directed to a method for the preparation of a liquid solution comprising DNase as active principle which comprises utilizing in said solution an amount of calcium ion and/or sugar that stabilizes said solutions from both thermally induced DNase aggregation and an amount of calcium ion that stabilizes said solutions from precipitation effects when said solutions are at less than neutral pH. In the latter instance, deamidation of the DNase is inhibited, a result of the lowered pH of the solution.

The present invention is further directed in different aspects to the solutions themselves comprising DNase as active principle and amounts of calcium ion, and to the use of these solutions for the treatment of disorders in which the biological activity of DNase can be exploited. As well, it is directed to methods for the use of such solutions in the preparation of further formulations comprising DNase as active principle such as subjecting said solutions to elevated temperatures, e.g. as in spray-drying techniques to produce pharmaceutically acceptable formulations of DNase in the form of a respirable DNase-containing powder, suspension or solution that is therapeutically effective when administered into the lung of an individual. Further, such solutions that are at less than neutral pH, in order to inhibit deamidation of the DNase, are rendered stable to (lower pH) induced precipitation when stored at temperatures at about ambient temperature or above.

The present invention is further directed to all associated embodiments thereof relating to the preparation and use of liquid solutions of DNase, which is essentially in monomeric form and/or inhibited in deamidation, and to stabilize against precipitation at pHs of less than neutral, employing the calcium cation to minimize thermal aggregation of the DNase.

The liquid solutions hereof comprise as essential components DNase as the biologically active principle and a source of calcium cation. In such solutions the DNase is in substantially monomeric form, and where such solutions are at a pH of less than neutral, deamidation of the DNase is inhibited, and in those instances, the solutions are stabilized against precipitation when stored at ambient or elevated temperatures.

The calcium ion source can be virtually any calcium salt supplied directly or formed in situ from a suitable calcium source that is pharmaceutically acceptable such as calcium chloride, in its various hydrated and anhydrous forms, calcium oxide and calcium carbonate. The calcium source for the calcium cation active component of the present liquid solutions of DNase is present generally at a concentration of from about 1 mM to about 1 M, and more preferably, from about 10 mM to about 100 mM.

The sugars may include, for example, $\alpha$-lactose monohydrate, mannitol, trehalose, sucrose, and the like. They are employed in concentrations generally of from about 50 to about 200 mg/ml., although concentrations outside of this range can also be used.

The solutions hereof may contain other components, such as excipients, with the only requirements being that such other components are pharmaceutically acceptable and do not interfere with the effect of calcium cation.

The solutions hereof can be used as such, or they can be used for the preparation of pharmaceutically acceptable formulations comprising DNase that are prepared for example by the method of spray-drying the liquid solutions hereof and collecting the spray-dried product as a dispersible DNase-containing powder that is therapeutically effective when administered into the lung of an individual. The calcium ion protecting effect applies to any situation in which rhDNase solutions are exposed to elevated temperature and/or where such solutions are at a pH of less than neutral.

For spray-drying the latter embodiment, attention is again directed to the co-pending U.S. application Ser. No. 08/206,020 filed Mar. 4, 1994 for the details concerning the spray drying procedure.

Present results would indicate that minimization of thermal-induced aggregation of DNase in solution can be achieved using lower temperatures in the range less than about 60° C. and protein concentrations of about less than 1 milligram per milliliter, with a pH of about 6 to 7 and a concentration of excipient of more than 10 millimoles (at the concentration of DNase given above).

Present results would indicate that minimization of precipitation of DNase solutions at a pH of less than neutral (in which solutions deamidation of the DNase is inhibited) results in solutions that can be pharmaceutically administered where such solutions are stable over long periods of time, remaining clear for ultimate such pharmaceutical administration.

The DNase formulations hereof are employed for enzymatic alteration of the viscoelasticity of mucus within the lung. Such formulations are particularly useful for the treatment of patients with pulmonary disease who have abnormal viscous, purulent secretions and conditions such as acute or chronic bronchial pulmonary disease, including infectious pneumonia, bronchitis or tracheobronchitis, bronchiectasis, cystic fibrosis, asthma, tuberculosis and fungal infections and the like. For such therapies, the novel formulations hereof are instilled generally by methods familiar to those skilled in the art into the bronchi of the individual being treated. The formulations hereof are particularly suited for the assured introduction into the lung of DNase such that a therapeutically effective amount of DNase is delivered to the individual by direct action in the lung.

DETAILED DESCRIPTION OF THE INVENTION

A. Definitions

By the term "DNase" or "human DNase" or "recombinant human DNase" or grammatical equivalents herein is meant a polypeptide having the amino acid sequence of human mature DNase as well as amino acid sequence variants thereof (including allelic variants) that are enzymatically active in hydrolyzing DNA. Thus, the terms herein denote a broad definition of those materials disclosed and prepared in the various patent applications cited above and incorporated herein by reference. It will be understood that the terms include both purified mixtures of deamidated and non-deamidated human DNase as well as purified forms of each.

By the term "excipient" herein is meant a pharmaceutically acceptable material that is employed together with DNase for the proper and successful preparation of a spray-dried formulation that results in therapeutic effect when administered into the lung of an individual patient. Suitable excipients are well-known in the art, and are generally described above and, for example, in the *Physician's Desk Reference,* the *Merck Index* and Remington's *Pharmaceutical Sciences.*

By the term "therapeutically effective" and grammatical equivalents thereof herein is meant dosages of from about 1 microgram to about 1 milligram of human DNase per kilogram of body weight of the individual being treated, administered within the pharmaceutical formulations hereof. The therapeutically effective amount of human DNase will depend, for example, upon the therapeutic objectives and the condition of the individual being treated. In all of that, the present invention provides as an essential component, formulations containing therapeutically effective amounts, the formulations being prepared such that they suitably provide such therapeutic effect when administered into the lung of the individual.

B. Preferred Embodiments/Examples
1. Thermally Induced Aggregation
a. Calcium Ion
Materials Stock solution: Recombinant Human DNase (rhDNase), 4.7 mg/ml, originally formulated in 150 mM NaCl and 1 mM $CaCl_2$, pH 7.0±1.0 was used as it is or adjusted as described.

Methods

Thermally induced aggregation was carried out by heating rhDNase solutions in 3 cc glass vials for lyophilization which were pre-equilibrated at the set temperatures in a water bath (Fisher Scientific). The temperature was controlled by a water circulator (Isotemp Immersion Circulator Model 730 Fisher Scientific) within an accuracy of ±0.2° C. as measured by a temperature probe (Thermistor Thermometer, Omega Engineering, Inc.). Solutions of rhDNase were pipetted into the vials, heated for different lengths of time, and transferred to an ice-bath to terminate any thermally induced reactions.

Size exclusion chromatography (SEC) was employed to quantify the amount of monomer and aggregates. When precipitation occurred (e.g., in cases of prolonged heating at high temperatures), the solutions were filtered (0.22 μm pore-size filters, ultra-low protein binding, Millex-GV). For the filtered samples, the % monomer or aggregate was corrected for the precipitated protein using the peak area of the control (i.e. time zero) sample. Depending on the concentrations, the solutions were then diluted with the SEC mobile phase to 1 mg/ml rhDNase for the measurement. The running conditions were:

Mobile phase: 5 mM HEPES, 150 mM NaCl, 1 mM $CaCl_2.2H_2O$, adjusted to pH 7.0 with NaOH. The absorbance was measured at 280 nm. Injection volume is 100 μl (1 mg/ml). Flow rate 1.0 ml/min. Running time was 20 min.

Figure 1:
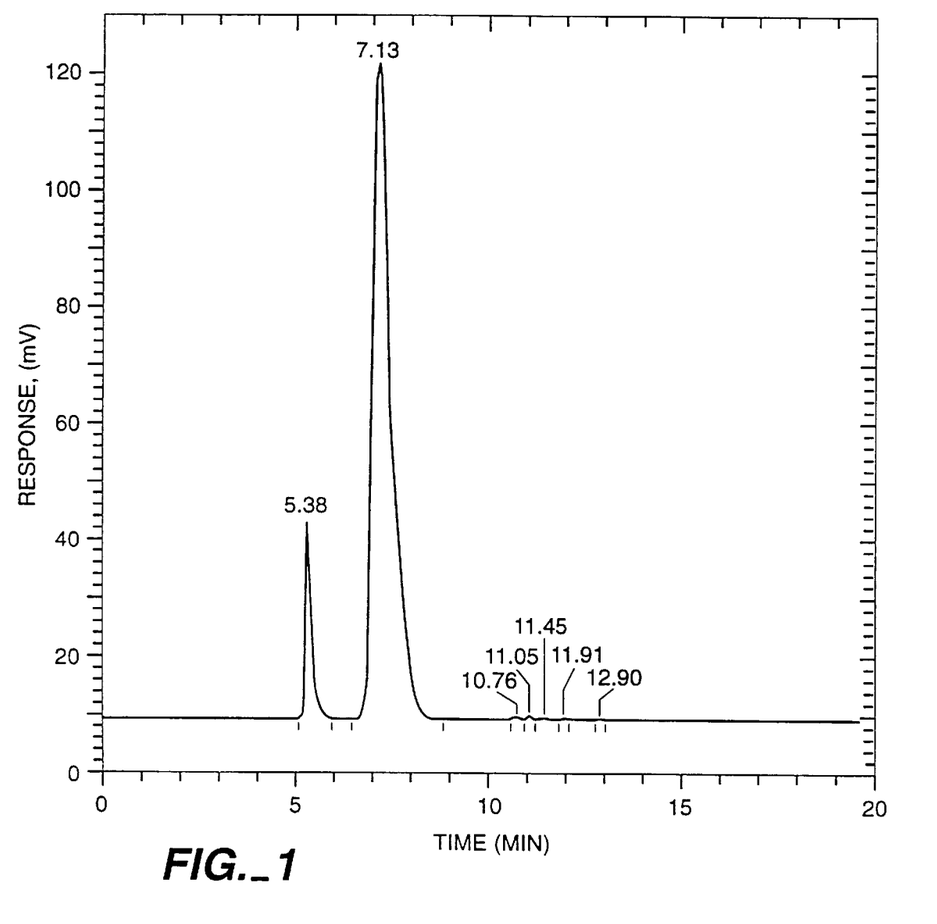
FIG. 1 is a size exclusion chromatogram of rhDNase. The sample was prepared from a solution of 4.7 mg/ml DNase, 150 mM sodium chloride, 1 mM calcium chloride, pH 6.7, heated at 65° C. for 60 seconds.

The amount of aggregates was expressed as a fraction of the peak area eluted at 5.3 min to the total area at 5.3 min and 7.1 min (FIG. 1). The peak areas were automatically integrated by the computer. In case of unsatisfactory integration (e.g. baseline shift), manual integration was employed.

EXAMPLE 1

Initial Study to Establish that Aggregation Takes Place Predominantly in Solution Rather than in the Solid State Stock solutions of rhDNase, after dialysis in water to remove excess salts, were either i) heated at 70–80° C. for 5 min or ii) lyophilized. The lyophilized powders were then either i) heated in the vial at 70–80° C. for 30 min or ii) pressed on a hot-plate at 80° C. for different lengths of time up to 3 min. The samples were reconstituted in water for the SEC measurements.

EXAMPLE 2

Effect of Calcium and Other Divalent Cations

Calcium and other divalent cations are known to stabilize bovine DNase I against denaturation. [Paulos et al., *The Journal of Biological Chemistry* 247, 2900 (1972)] The possible stabilizing effect of the ion on the thermal aggregation of rhDNase was studied at 65° C. Predetermined amounts of calcium chloride were dissolved in the stock rhDNase solutions (pH 6.7) to give higher calcium concentrations of 9 and 106 mM as compared to 1 mM in the original solution.

For the other divalent cations, known amounts of analytical grade $ZnCl_2$, $MnCl_2.4H_2O$, and $MgCl_2.6H_2O$ were respectively dissolved in the DNase stock solution to give a concentration of 100 mM of the cations.

The study was carried out at 65.3±0.20° C. As precipitation occurred in some of the solutions, those samples were filtered (0.22 μm filter unit, Millex-GV 4) before SEC analysis.

Chemical Nature of the Soluble Aggregates

The chemical nature (covalently bond or disulfide linkage) of the aggregates was analyzed by SDS-PAGE (Sodium Dodecyl Sulfate Polyacrylamide Gel Electrophoresis). Two fully aggregated samples were measured. A 10 μg (in 10 μl) of 1 mg/ml rhDNase load was used. The gels were stained with Coomassie blue.

Thermally Induced Aggregation of rhDNase in the Solution and Solid-state

Table 1 shows that heating the rhDNase powders results in less than 1% aggregated rhDNase whereas in solution the protein can fully aggregate quite rapidly. Thus, thermally induced aggregation occurs much more significantly in solution than in the solid state. This suggests that the aggregates found in the spray-dried DNase powders were formed in the solution state in droplets or while the powder still contains a high moisture content.

Effect of Calcium and other Cations (at pH 6.4±0.2)

Divalent cations were reported to affect the stability of bovine DNase structure.

Figure 2:
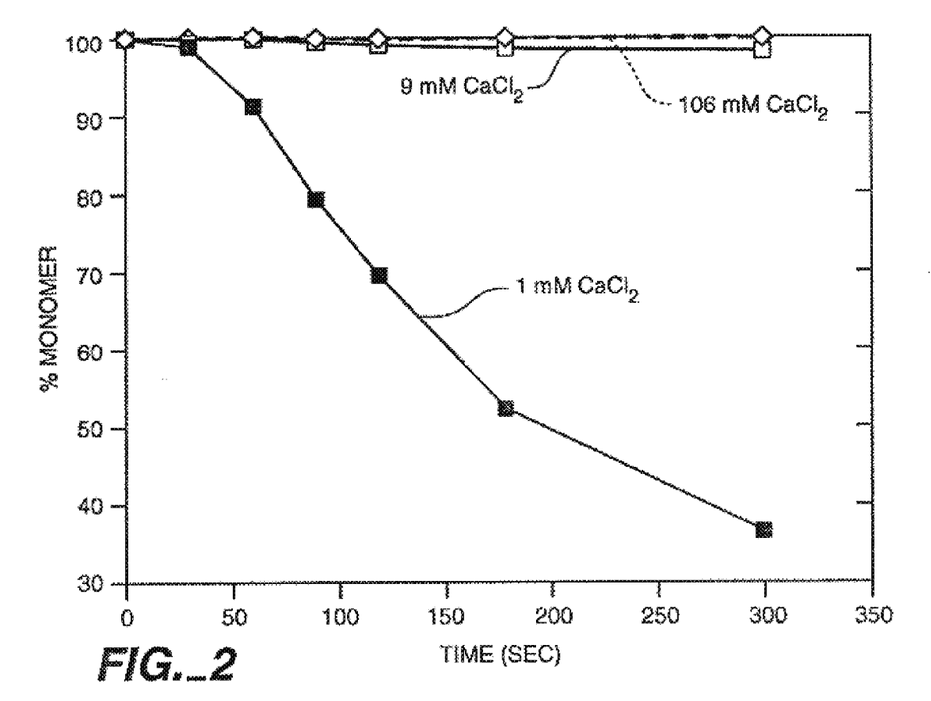
FIG. 2 shows the protective effect of calcium ion against thermally induced aggregation of rhDNase in solution at 65° C. (4.7 mg/ml rhDNase, 150 mM sodium chloride, pH 6.5 to 6.7).

FIG. 2 and Table 2 indicate the effect of calcium ions. At 9 mM $CaCl_2$, the protection against thermal aggregation at 65° C. for 5 min is 98%; at 100 mM $CaCl_2$ it offers complete protection. Other divalent cations such as $Mn^{2+}$, $Mg^{2+}$ and $Zn^{2+}$ (chloride as the same anions) at 100 mM did not give such protection as $Ca^{2+}$. In fact, $Zn^{2+}$ precipitates the protein even at room temperature (Table 3). Thus, rather than an ionic strength effect, calcium ions appear to specifically bind to the protein preventing aggregation.

Chemical Nature of the Aggregates

Figure 3:
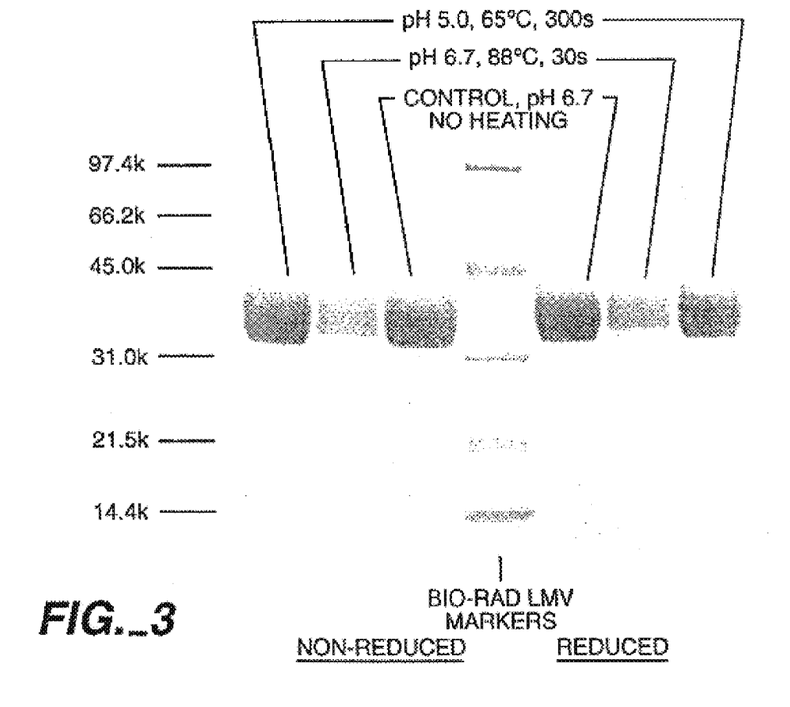
FIG. 3 shows an SDS-PAGE gel of thermally induced aggregated rhDNase (4.7 mg/ml rhDNase, 150 mM sodium chloride, 1 mM calcium chloride, pH 6.7). The normal molecular weights of the marker proteins are indicated.
Figure 4A:
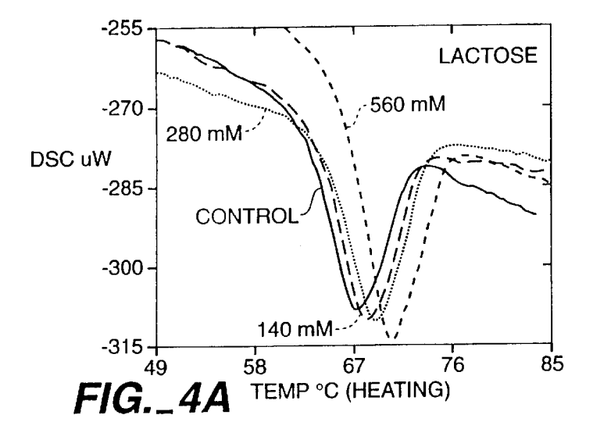
FIGS. 4a–d are differential scanning calorimetry (DSC) thermograms of rhDNase showing the effects of sugars at various concentrations.
Figure 4B:
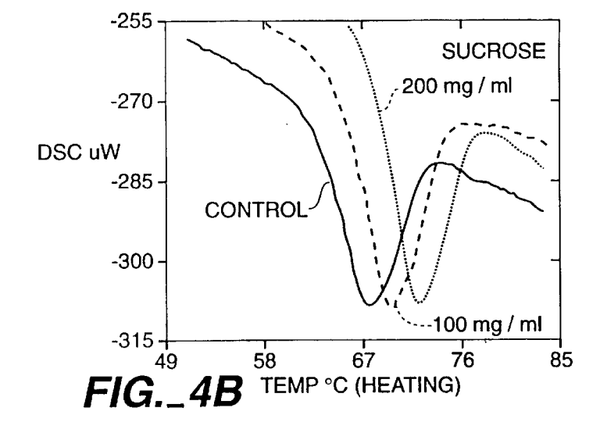
Figure 4C:
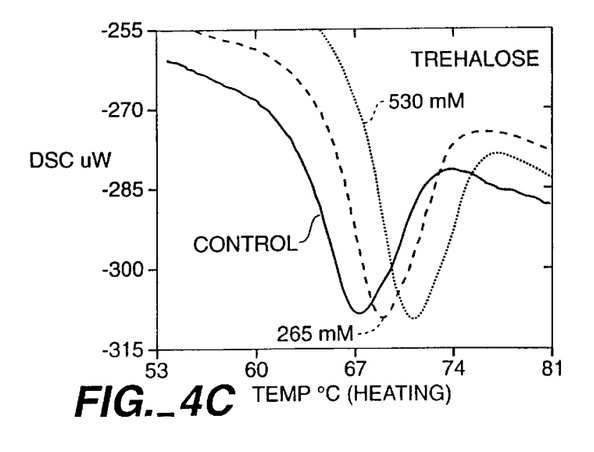
Figure 4D:
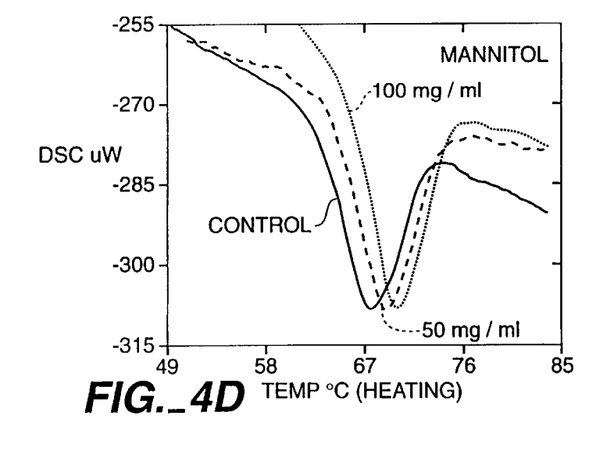
Figure 4E:
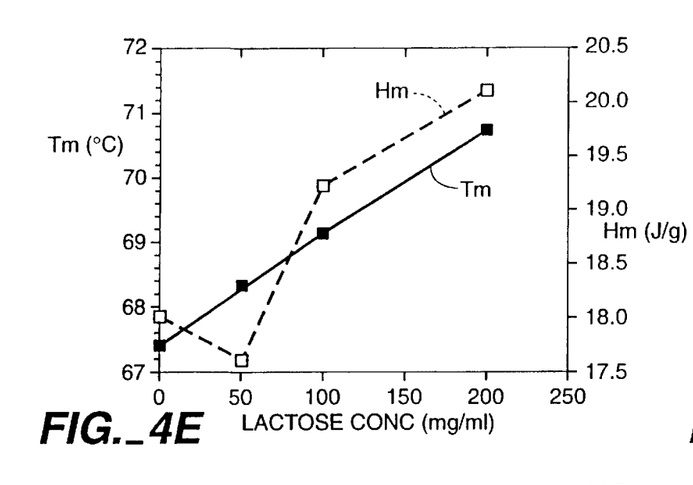
FIGS. 4e–h shows the denaturation or melting temperature (Tm) and enthalpy (Hm) of rhDNase plotted versus sugar concentration.
Figure 4F:
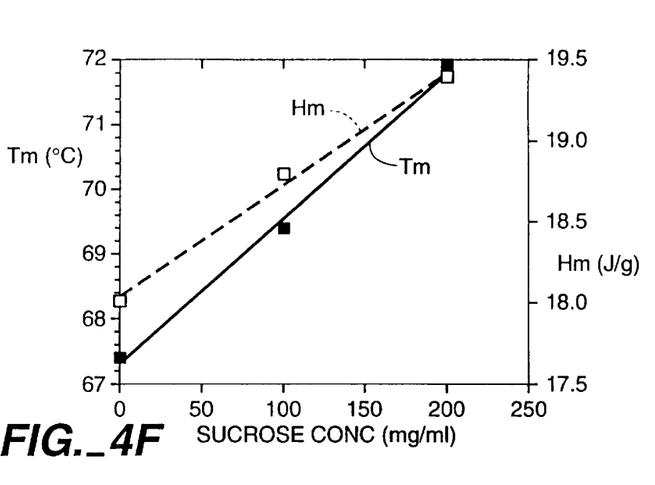
Figure 4G:
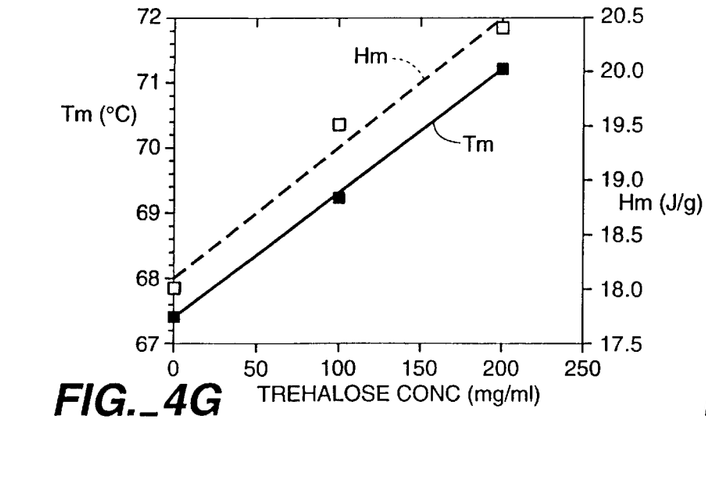
Figure 4H:
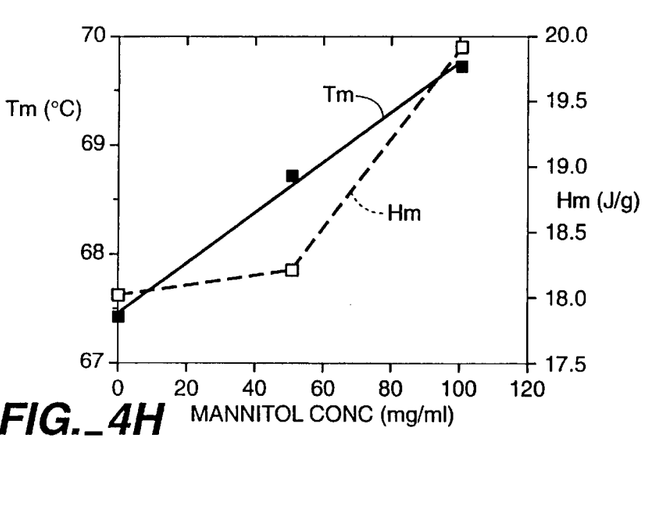

The SDS-PAGE results (FIG. 3) show that the band pattern of the aggregated samples are the same as the non-aggregated ones, indicating that the aggregates dissociate in the SDS. Thus, the aggregates are not covalent or linked by disulfide bond.

TABLE 1

Thermally Induced Aggregation of rhDNase in the Solution and Solid-state

| Sample | % Monomer |
|---|---|
| Solution, Control[1] | 99.92 |
| Solution, Lyophilized[2] | 99.62 |
| Solution, Heated & Lyophilized[3] | 0.88 |
| Solution, Lyophilized & Heated[4] | 98.96 |
| Solution, Lyophilized & Heated[5] | 99.33 |
| Solution, Lyophilized & Heated[6] | 99.02 |
| Solution, Lyophilized & Heated[7] | 99.01 |

Notes:
[1]Solution after dialysis in water as a control with no further treatment
[2]Solution 1 lyophilized to powder
[3]Solution 1 heated to 70–80° C. for 5 min, then lyophilized
[4]Lyophilized powder of 2 heated to 70–80° C. in a water bath for 30 min
[5]Lyophilized powder of 2, pressed on a hot-plate at 80° C. for 30 sec
[6]Lyophilized powder of 2, pressed on a hot-plate at 80° C. for 1 min
[7]Lyophilized powder of 2, pressed on a hot-plate at 80° C. for 3 min.

TABLE 2

Effect of Calcium Ion on the Thermally Induced Aggregation of rhDNase in Solutions at 65° C. (4.7 mg/ml, 150 mM NaCl, pH 6.6 ± 0.1

| | % Monomer | | |
|---|---|---|---|
| Time (s) | 1 mM $Ca^{2+}$ | 9 mM $Ca^{2+}$ | 106 mM $Ca^{2+}$ |
| 0 (control) | 99.64 | 100.0 | 99.97 |
| 30 | 98.96 | 99.92 | 99.98 |
| 60 | 91.14 | 99.95* | 99.96 |
| 90 | 79.16 | 99.78 | 99.90 |
| 120 | 69.05 | 99.45 | 99.81 |
| 180 | 51.87 | 99.25 | 99.96 |
| 300 | 36.63 | 98.17 | 99.95 |

TABLE 3

Effect of Divalent Cations on the Thermally Induced Aggregation of rhDNase in Solutions (4.7 mg/ml rhDNase, 150 mM NaCl, 1 mM $CaCl_2$, pH 6.2–6.5) at 65° C.

| | % Monomer | | |
|---|---|---|---|
| Time (s) | $Mn^{2+}$ | $Mg^{2+}$ | $Zn^{2+}$ |
| 0 (control) | 99.99 | 99.05 | <19 (ppt'd) |
| 30 | 99.57 | — | — |
| 90 | <70 (ppt'd) | — | — |
| 120 | <47 (ppt'd) | <74 (ppt'd) | — |
| 180 | <31 (ppt'd) | <73 (ppt'd) | — |

Note:
the % monomer in the precipitated (ppt'd) samples were only estimated values as the monomer peak of the control samples went offscale in the chromatogram. The actual % monomer would therefore be even lower. These results should be compared to the low and high calcium effects in the previous table (Table 2).

b. Sugars

Materials and Methods

A stock rhDNase solution of 20 mg/ml was prepared from a starting solution (rhDNase 6.4 mg/ml, 150 mM NaCl, 1 mM $CaCl_2$) by concentration in an Amicon deafiltration cell followed by dialysis in Milli-Q water to remove the salts. The solutes (additives) which were studied for their effects on thermal stability of rhDNase were: α-lactose monohydrate (Sigma, lot 72H0563), mannitol (Sigma, lot 31H0181), trehalose (Sigma, lot 112H3903), sucrose (AR, Mallinckrodt, lot 8360 KBTA).

Differential Scanning Calorimetry (DSC)

DSC was carried out on a highly sensitive differential scanning calorimeter (DSC 120, Seiko Instruments) which has a detectability <2 $\mu$W. The solutions were sealed in a silver sample pan (60 $\mu$l) with water used as the reference. Preliminary runs were done on a series of pure rhDNase solutions using scanning rates ranging 0.1–2.0° C./min. Generally, a fast heating rate will result in a broader peak with a shift in the baseline, while slow heating will give a low signal to noise ratio. With regard to the protein concentration, while low concentration will not give sufficient DSC signal, high concentration will facilitate aggregation. The optimal protein concentration and heating rate were found to be around 10 mg/ml and 1.2° C./min, respectively, which were subsequently employed throughout this study.

Preparation of rhDNase Solutions Containing Additives

Aqueous solutions of different additives were prepared by dissolving a known amount of the solute in Milli-Q water. The solution pH was adjusted using diluted NaOH or HCl to a value between 6 and 7 (this will give rise to a difference within 1.0° C. in the $T_m$ and 0.5 J/g in $H_m$, see Results and Discussion). 70–100 $\mu$l of the 20 mg/ml rhDNase stock solution were then mixed with an equal volume of additive solutions (which was substituted by pure water for the control rhDNase samples). The final pH of the solutions was measured as 6.3 to 7.0. No buffer was added in order to avoid possible interactions of the buffer species with rhDNase and/or additives.

Proteins unfold or 'melt' at elevated temperatures and usually involve endothermic heat changes. For rhDNase, the apparent denaturation temperature ($T_m$) and enthalpy (Hm) of 10 mg/ml rhDNase in pure water at pH 6.8 were found to be 67.4±0.3 and 18.0±0.2 (n=4), respectively, values typical of globular proteins.

Effects of Sugars

FIGS. 4a–d show the protective effects of different sugars (disaccharides: lactose, sucrose and trehalose, monosaccharide; mannitol) on rhDNase against thermal denaturation. In general, both the $T_m$ and $H_m$ appear to increase monotonically with the sugar concentration (FIGS. 4e–h). The effects could be explained thermodynamically. Addition of sugars (as stabilizers) increases the chemical potential of the protein (both native and denatured state). However, because of the larger surface area of contact between the unfolded protein and solvent, the increase is higher (and thus more favorable) for the denatured state than the native state. Thus, the native state is stabilized because thermodynamically it will be more unfavorable to move to the denatured state.

2. Liquid Solution Stabilization

Figure 5:
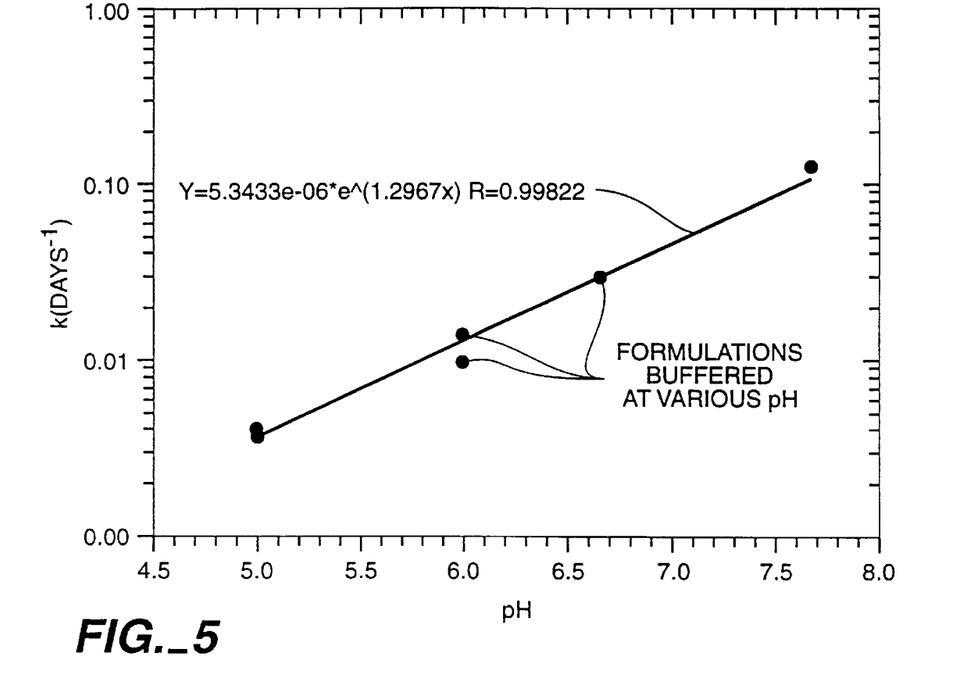
FIG. 5 shows the effect of pH on rates of deamidation of rhDNase at 37° C. by tentacle ion-exchange chromatography.

The major route of degradation for rhDNase is deamidation. Deamidation correlates with loss in activity as assessed by the methyl green activity assay. The rate of deamidation was also found to be highly dependent on the pH of the formulation (FIG. 5). In particular, as the pH decreases, the rate of deamidation can be minimized even at higher storage temperatures.

Figure 6A:
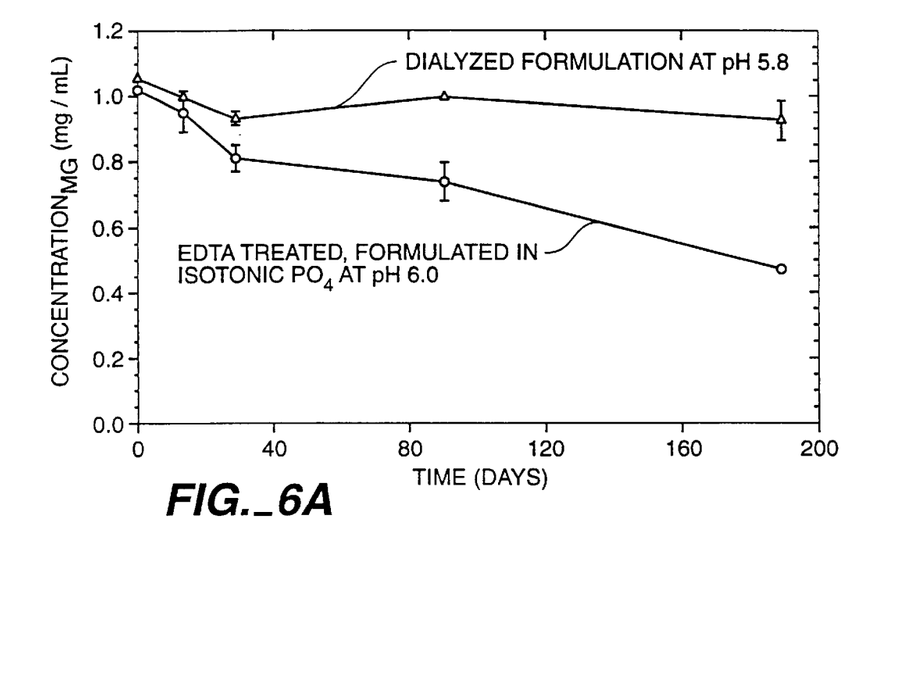
FIG. 6 shows the effect of calcium on stability of rhDNase: 1 mg/ml, 2 ml in 5 cc glass vial with siliconized Teflon stopper at 25° C. storage.
Figure 6B:
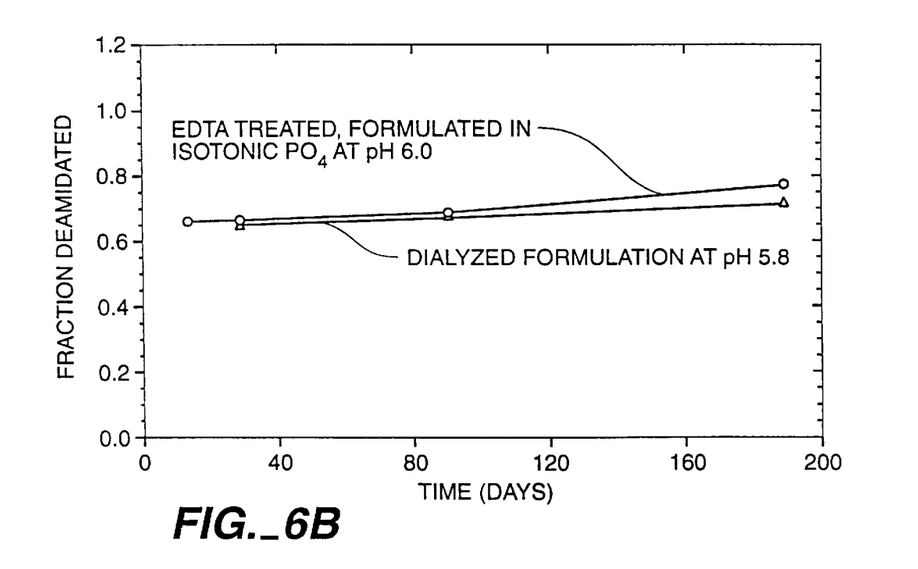

The importance of $Ca^{++}$ in the stabilization of rhDNase was demonstrated in an experiment in which rhDNase 1 mg/mL in 150 mM NaCl, 1 mM $CaCl_2$) was treated with 1 mM EDTA to remove the exogenous $Ca^{++}$ bound to the protein, and formulated into phosphate buffer at pH 6. Analysis of $Ca^{++}$ indicated there were still 1 to 1.5 moles $Ca^{++}$/mole of rhDNase. The activity of rhDNase in this formulation was shown to be less stable than the original formulation in 1 mM $CaCl_2$ as shown in FIG. 6. The percent deamidation was about the same for both formulations suggesting that the decrease of activity was not related to different rates of deamidation in the formulation (see inset, FIG. 6). The conclusion was that $PO_4$ was competing with rhDNase for calcium resulting in a less stable protein. As the bulk rhDNase in current formulation is being concentrated, the ratio of $Ca^{++}$ to rhDNase decreases accordingly. Therefore, it was reasoned that supplementing the current formulation with increasing amounts of $Ca^{++}$ may enhance the stability of rhDNase at higher concentrations.

Materials & Methods

Preparation of 50 mg/mL rhDNase in 150 mM NaCl. 1 mM $CaCl_2$ pH 5 & 6. by Acid Titration rhDNase, (4.7 mg/mL, 150 mM NaCl, 1 mM $CaCl_2$) was concentrated to ~50 mg/ML at 2–8° C. by Amicon ultrafiltration using a YM10 membrane. The concentrated rhDNase solution was divided into two equal aliquots. The first aliquot was adjusted to pH 6 with 1N HCl. The second aliquot was adjusted to pH 5. Both solutions were filtered through a 0.2 $\mu$m filter unit and sterile filled into 3 cc glass vials with a nominal volume of 1 mL. The samples were stored at −70°, 2–8°, 15°, 25° and 37° C. The stability of these rhDNase solutions was assessed over 6 months by color/clarity, pH, UV for protein concentration, methyl green (MG) activity assay, size-exclusion chromatography for aggregates, and tentacle ion-exchange chromatography for percent deamidation. SDS-PAGE was performed initially to confirm the presence of aggregates.

Preparation of 50 mg/mL rhDNase in 150 mM NaCl. 0–200 mM $CaCl_2$. pH 5. by Acid Titration The high concentration rhDNase formulation was prepared as described above. After concentration the rhDNase was dialyzed into solutions containing 150 mM NaCl, 10–200 mM $CaCl_2$, at 2–8° C. for 36 hours with two buffer changes. Two aliquots of the same concentrated rhDNase were dialyzed against 1 mM EDTA. One aliquot was then further dialyzed into 150 mM NaCl only, and the other into 150 mM NaCl, 1 mM $CaCl_2$. After dialysis, the solutions were adjusted to pH 5 with 1 N HCl. All final solutions were filtered and sterile filled into 3 cc glass vials with 0.5 mL nominal volume. The stability of these solutions was monitored as above at 37° C. for up to 6 months for the 0–50 mM $CaCl_2$ and up to two months for >50 mM $CaCl_2$ samples.

Preparation of 50 mg/mL rhDNase in 1 mM Acetate Buffer. 1, 50 and 100 mM $CaCl_2$ at pH 5 & 5.2. by Dialysis rhDNase was concentrated to 50 mg/mL from the bulk rhDNase (4.7 mg/mL) as described above. The concentrated rhDNase was buffer exchanged into 1 mM NaOAc, 1, 50 or 100 mM $CaCl_2$ isotonic with NaCl at either pH 5 or 5.2 by dialysis at 2–8° C. for 36 hours. The dialyzed solutions were filtered and sterile filled into 3 cc glass vials with 0.5 mL nominal volume. The samples were stored at 37° C. and the stability of rhDNase was assessed periodically for 1 month with the assays as described below.

Effect of $Ca^{++}$ and Ionic Strength on the Physical Stability of 50 mg/mL rhDNase at pH 5 at 37° C.

50 mg/mL rhDNase solutions at ionic strengths ranging from 0.153 M (150 mM NaCl, 1 mM $CaCl_2$) to 3.15 M (150 mM NaCl, 1 M $CaCl_2$ and 3.15 M NaCl, 1 mM $CaCl_2$) were prepared by Amicon concentration and dialysis. The solutions were adjusted to pH 5 by acid titration. Similarly, another set of 50 mg/mL rhDNase solutions buffered at pH 5 with ionic strengths from 0.154 M (1 mM NaOAc, 150 mM NaCl, 1 mM $CaCl_2$) to 0.226 M (1 mM NaOAc, 75 mM NaCl, 50 mM $CaCl_2$ and 1 mM NaOAc, 222 mM NaCl, 1 mM $CaCl_2$) were prepared. The samples were stored at 37° C. and visually inspected at T=0,1 and 3 days Determination of Ca$^{++}$ Content in rhDNase Solutions The Ca$^{++}$ contents were analyzed by Atomic Absorption (AA) according to and by LC (ion chromatography equipped with a conductivity detector. rhDNase samples were diluted with Milli-Q water to 1–5 ppm for AA analysis and to 30–50 μg/mL for LC analysis. rhDNase in current formulation at 1 mg/mL (S9847A, 150 mM NaCl, 1 mM CaCl$_2$), bulk rhDNase at 4.7 mg/mL, 5.9 mg/mL, and 10 mg/mL, and the concentrated rhDNase at 50 mg/mL were analyzed by both methods and compared. rhDNase samples treated with 1 mM EDTA were also analyzed.

Assay Methods (1) Color and Clarity: All samples were visually inspected for color and particulates.
(2) pH: The pH measurement was performed with a Radiometer pHM84 meter equipped with a microelectrode (MI-410, Microelectrodes, Inc.,). Samples (20 uL) were transferred into 0.5 mL eppendorf tubes for measurement at ambient temperature.
(3) UV: The concentration of the protein was determined by ultraviolet absorption spectroscopy from 240–400 nm using an HP8451A spectrophotometer. Appropriate rhDNase excipients were used as references. The absorbance at 280 nm was corrected for offset or light scattering by subtracting the absorbance value at 320 nm. The concentration of the protein was determined from the corrected absorbance at 280 run using an absorptivity of 1.6 cm$^{-1}$ (mg/mL)$^{-1}$.
(4) Methyl Green Activity Assay: The activity of the protein was determined by the Methyl Green assay. The samples were diluted to assay range with assay diluent in duplicate runs. rhDNase reference material frozen at −70° C. was used as a reference control and the results were normalized to this control to account for the inter-assay variation.
(5) Size exclusion chromatography (TSK 2000): To determine the presence of aggregates and fragments.
(6) Tentacle ion exchange chromatography: To determine the % deamidation in the protein.
(7) SDS-PAGE (Oakley silver stain): To determine the presence of fragments and covalent aggregates.
(8) Ca$^{++}$ analysis, (AA) and (LC): To determine the total Ca$^{++}$ content in rhDNase.

Effect of pH on the Stability of High Concentration rhDNase rhDNase in current formulation (150 mM NaCl, 1 mM CaCl$_2$) was concentrated to ~50 mg/mL at 2–8° C. with Amicon ultrafiltration using a YM10 membrane. The concentrated solution was clear to slightly yellow. Precipitation occurred upon acid titration to pH 5 but was not noticeable at pH 6. The solution was clarified by filtration but precipitated after one day at pH 5 and five days at pH 6 at 37° C. The precipitate could be solubilized in strong base. However, in a control experiment where there was no precipitation initially, addition of strong base to the protein caused denaturation creating high molecular weight aggregates. SDS-PAGE (not shown) of the precipitate confirms the presence of high molecular weight aggregates and fragments. Both have very intense bands that spread along the whole lane on the gel.

Figure 7:
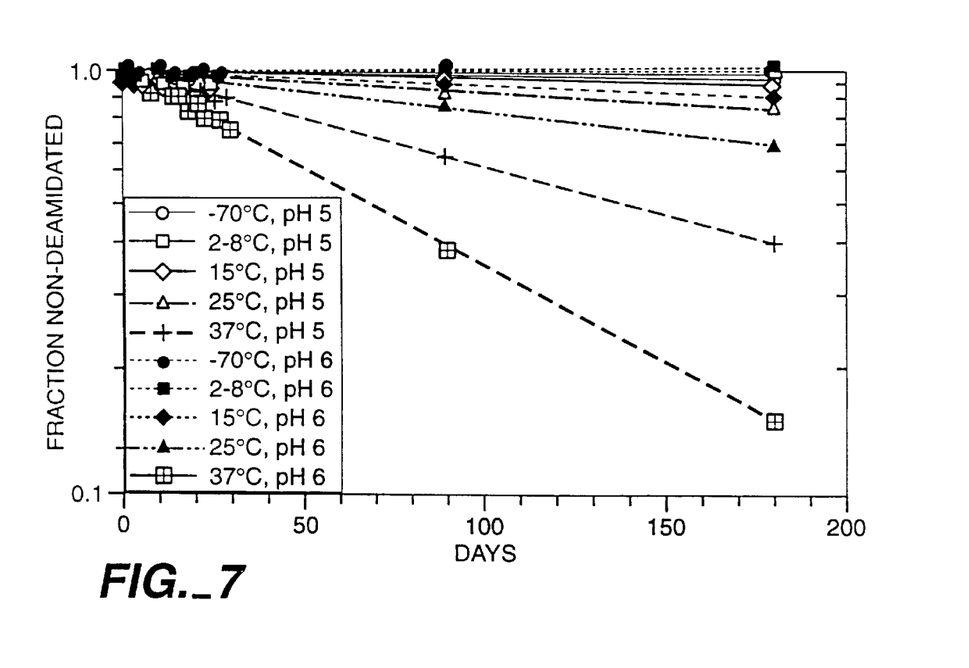
FIG. 7 illustrates the kinetics for deamidation of rhDNase: 50 mg/ml in 150 mM NaCl, 1 mM $CaCl_2$, pH 5 and 6.
Figure 8:
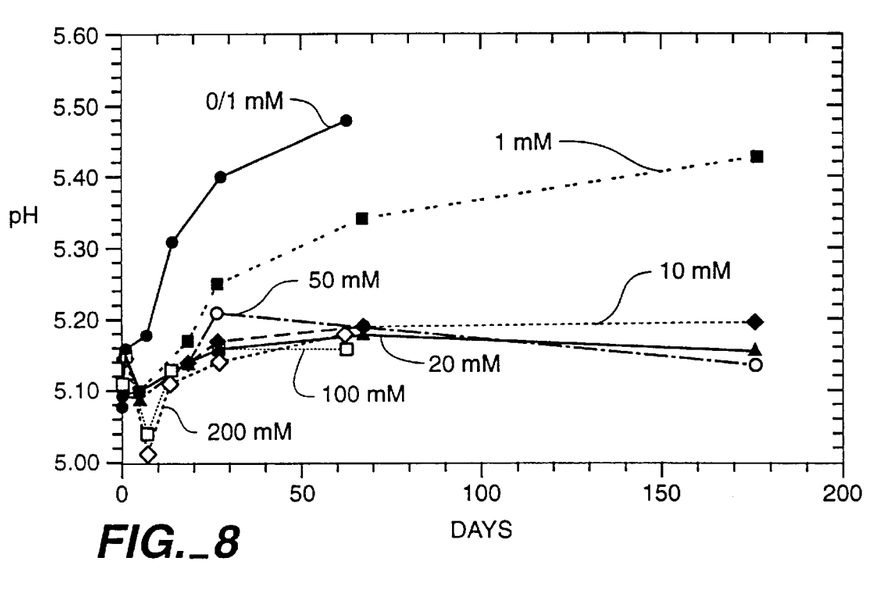
FIG. 8 shows pH variance of rhDNase: 50 mg/ml in 150 mM NaCl, 0–200 mM $CaCl_2$, pH 5 at 37° C.

The pseudo first order kinetics for deamidation of rhDNase at 50 mg/mL in 150 mM NaCl, 1 mM CaCl$_2$ at pH 5 & 6 (by acid titration) shows that the deamidation rate was lower at pH 5 than at pH 6 at higher storage temperatures (>25° C). See FIG. 7. These pseudo first order rate constants were in good agreement with the rate constants previously determined for buffered rhDNase solutions at 1 mg/mL (Table 4). This result shows that deamidation of rhDNase is independent of protein concentration, but is highly dependent on the pH of the formulation. Since the rate of deamidation is pH dependent, it is important to maintain the pH of the formulation during storage.

pH variance of 50 mg/mL rhDNase solutions containing various amount of Ca$^{++}$ in 150 mm NaCl, pH 5 at 37° C. for 6 months was determined. See FIG. 8. At this temperature, the pH of the formulations with <10 mM CaCl$_2$ increased gradually with time while the formulations with >1 mM CaCl$_2$, the pH remained constant. This suggests that increasing Ca$^{++}$ may provide a more stable pH at higher storage temperature. The increase in pH of the formulations at 37° C., containing 1 mM or less CaCl$_2$, may be due to precipitation of rhDNase. Since the protein is the major buffering component in these formulations, a decrease in protein concentration may lower the buffering capacity of the formulation. A formulation where rhDNase was first treated with 1 mM EDTA and then subsequently dialyzed back into 1 mM CaCl$_2$ is represented by the symbol 0/1 mM CaCl$_2$ in FIGS. 8 and 9. This formulation should behave the same as the original formulation of 1 mM CaCl$_2$.

Effect of Ca$^{++}$ on the Stability of High Concentration rhDNase

Figure 9:
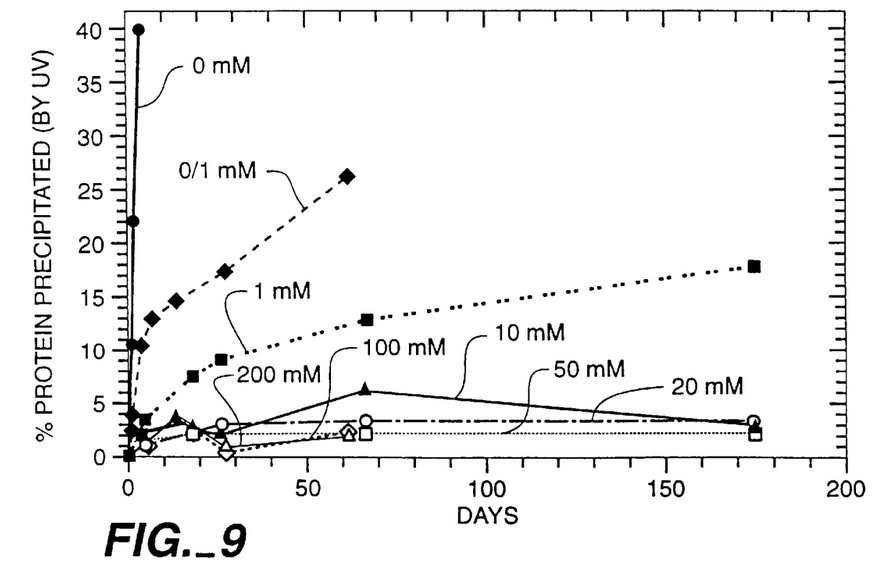
FIG. 9 demonstrates the physical stability of rhDNase, 50 mg/ml in 150 mM NaCl, 0–200 mm $CaCl_2$, pH 5 at 37° C.

Calcium plays a major role in the stabilization of rhDNase. Removal of Ca$^{++}$ by treatment with EDTA resulted in an unstable formulation at 50 mg/mL at pH 5 and 37° C. (FIG. 9). The percent of precipitated protein was determined indirectly by measuring the decrease in rhDNase concentration by UV spectroscopy. The addition of CaCl$_2$ (up to 200 mM) greatly stabilized the formulation by decreasing the amount of precipitated rhDNase (40% vs. ~2%) even after 150 days at 37° C. The cloudiness can be distinguished by visual examination. Nevertheless, the rates of deamidation for rhDNase at 50 mg/mL are independent of Ca$^{++}$ concentrations for up to 6 months at 37° C.

Effect of Direct Acid Titration on rhDNase

After concentration of the bulk rhDNase by ultrafiltration, additional 10–200 mM CaCl$_2$ is dialyzed into the 50 mg/mL rhDNase at 2–8° C. The dialyzed solutions become turbid during acid titration to pH 5 with HCl but these solutions are less cloudy than the high concentration rhDNase formulation containing 1 mM CaCl$_2$ when titrated the same way. The precipitates are found to be protein.

It is conceivable that addition of HCl may result in large local pH decreases before sufficient mixing of the solution is attained. Exposure to local drop in pH decrease may denature some of the rhDNase resulting in the observed precipitation. The denatured rhDNase might also serve as a nucleating species for further association, and ultimately increased precipitation over time. The following experiment was set up to study this matter further. The supernatants of rhDNase solutions at 50 mg/mL containing 1 to 200 mM CaCl$_2$ in 150 mM NaCl, pH 5 (by acid titration) were obtained by centrifugation after the samples were stored at 37° C. for 30 days. The clear supernatants were removed from the original solutions, placed into clean glass vials and stored at 37° C. for visual inspection. Small amounts of precipitate were observed only in the 1 mM CaCl$_2$ formulation after 7 days of storage (Table 5). This suggests that removal of denatured rhDNase, which may act as a nucleating site for aggregate formation, inhibits the rate of formation of further precipitate. Increasing Ca$^{++}$ concentration to >1 mM helps to minimize the denaturation of rhDNase caused by direct acid titration.

The local pH hypothesis was tested by avoiding direct acid titration of the formulation. After concentration of the rhDNase with an Amicon stirred cell, the formulation was dialyzed into 150 mM NaCl, 1 mM CaCl$_2$ at pH 4.7. The final rhDNase was a clear solution with a pH of 5.0, whereas, direct titration to pH 5 resulted in a turbid solution. This further supports the idea that precipitation of protein during acid titration to pH 5 is due to a local pH effect. No dimers or soluble aggregates were detected by size-exclusion chromatography for the 50 mg/mL rhDNase solutions prepared by dialysis at pH 5.

Inclusion of Buffer into the Formulation

Figure 10:
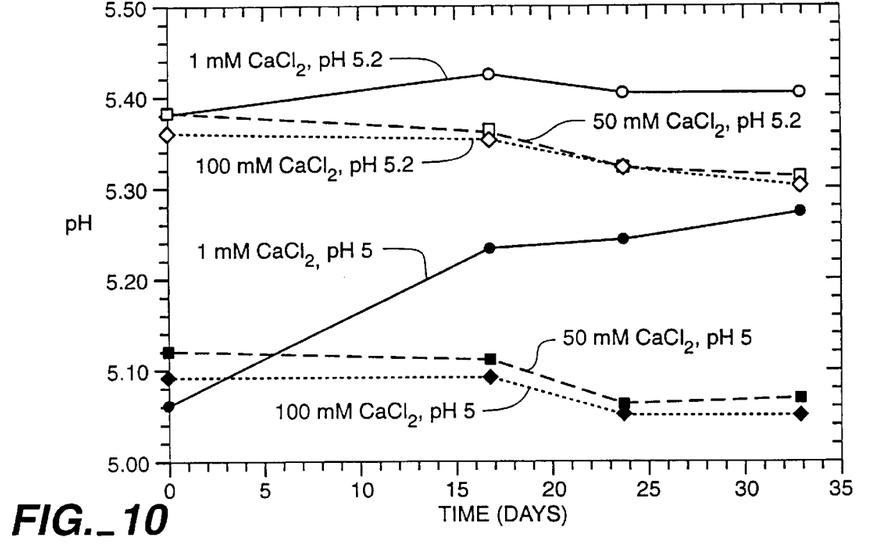
FIG. 10 shows the physical stability of rhDNase, 50 mg/ml in 1 mM NaOAc buffers, pH 5 and 5.2 at 37° C.
Figure 11:
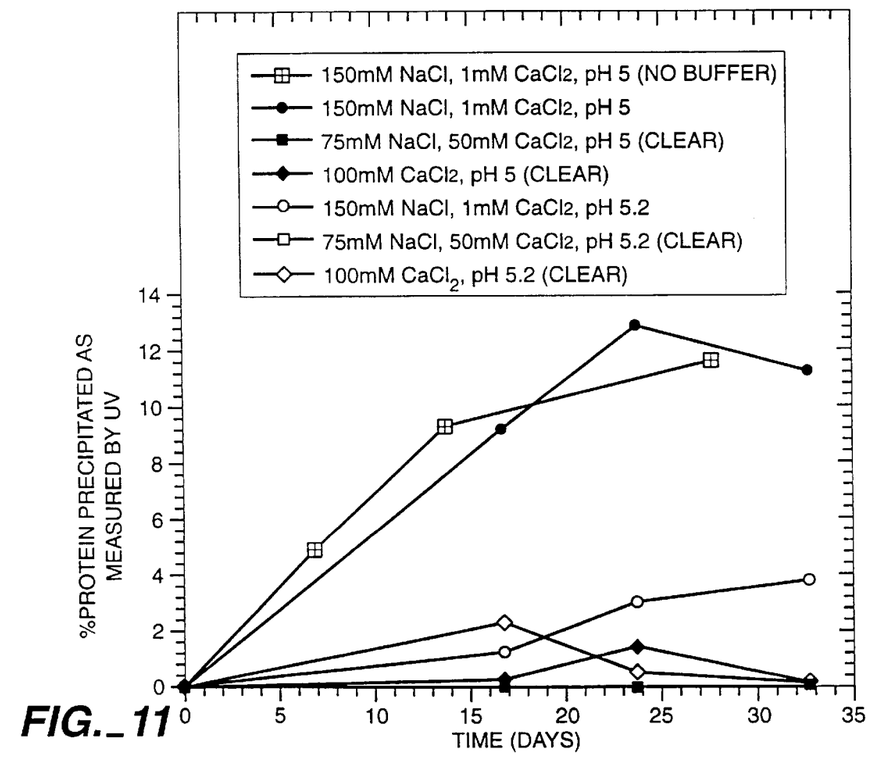
FIG. 11 shows pH of 50 mg/ml rhDNase in 1 mM acetate buffers 1–100 mM $CaCl_2$, isotonic with NaCl at pH 5 and 5.2, 37° C.

A small amount of acetate buffer (1 mM), together with 50 mM or 100 mM $CaCl_2$ isotonic with NaCl at pH 5 or 5.2, was supplemented into the formulation by dialysis of the concentrated rhDNase in current formulation. All the buffered solutions with >1 mM CaCl2 remain clear for up to a month at 37° C. (FIG. 10). The high concentration rhDNase in 1 mM NaOAc, 150 mM NaCl, 1 mM $CaCl_2$, shows a significant decrease in the amount of precipitation upon storage at 37° C. when the pH is increased from 5.0 to 5.2, indicating that the precipitation of protein is very pH dependent. Increasing the level of $Ca^{++}$ to 50 mM or more, results in formulations which do not precipitate even after 1 month at 37° C. at pH 5 & 5.2. During the preparation of these high concentration rhDNase solutions, an immediate rise in pH after dialysis is noted especially for the pH 5.2 samples which has a pH of almost 5.4 (FIG. 11). At pH 5.2, the 1 mM acetate buffer does not have much buffering capacity, and the pH rises regardless of calcium concentration.

Table 6 shows that, based on color and clarity, >10 mM $CaCl_2$ is required to maintain the physical stability of the high concentration rhDNase at pH 5 for long term storage at 37° C. A more effective calcium concentration probably lies in the 25–50 mM range.

Acetate buffers ranging from 0.25 mM to 1 mM was tested to see which concentration is adequate for buffering of the 50 mg/mL rhDNase containing 1–50 mM $CaCl_2$ isotonic with NaCl at pH 5 (by dialysis), stored at 37° C. The results are given in Table 7. Based on pH, color and clarity, the 1 mM NaOAc and 50 mM $CaCl_2$ formulation gives constant adequate buffering at the desired pH (5.0±0.20) over a period of 28 days. There is a slight rise in pH after dialysis. Therefore, the buffer used to prepare high concentration rhDNase should begin with the same buffer at 0.1–0.2 pH unit lower than the expected pH in the final formulation.

Effect of Ionic Strength on the Physical Stability of High Concentration rhDNase The protective effect of addition of calcium (to prevent precipitation of protein at 37° C.) beyond 1 mM could be the result of high ionic strength rather than a specific calcium effect. Table 8 shows that this protective effect can be achieved at very high ionic strength (I=3.1 5 M) in the formulation such as 1 M $CaCl_2$ and 150 mM NaCl or 3.15 M NaCl and 1 mM $CaCl_2$ alone. For an isotonic solution at a reasonable ionic strength, increasing $Ca^{++}$ to 50 mM is definitely beneficial to the formulation at high concentration.

$Ca^{++}$ Binding Study of rhDNase rhDNase in final vial 1 mg/mL, in bulks 5.9 mg/mL; 10 mg/mL; 4.7 mg/mL, and concentrated rhDNase 50 mg/mL in current formulation of 150 mM NaCl, 1 mM $CaCl_2$ were submitted for calcium analysis by AA and LC (ion chromatography equipped with a conductivity detector). The concentrated rhDNase supplemented with 10–200 mM $CaCl_2$ and the EDTA treated rhDNase were also analyzed. The expected calcium concentration would range from 0–200 mM. The results (Table 9) show both AA and LC methods are comparable. One sample (10 mg/mL shown with an asterisk) was also analyzed by Inductive Coupled Plasma—Atomic Absorption Spectroscopy (ICP-AAS) for total calcium. The results are in good agreement with the AA method.

One notable observation is the excess of $Ca^{++}$/mole of rhDNase found in all cases. In all the formulations, regardless of rhDNase and $Ca^{++}$ concentration, there are always 4 to 5 more moles of $Ca^{++}$/mole of rhDNase than expected (Table 9). The EDTA treated rhDNase still has 1–1.5 moles of $Ca^{++}$/mole of rhDNase. This suggests there is one tightly bound $Ca^{++}$ to the protein, and the remaining represents weakly bound $Ca^{++}$. The 0/1 mM $CaCl_2$ formulation (EDTA treatment followed by dialysis versus 1 mM $CaCl_2$) is found to contain 1 mole of $Ca^{++}$/mole of rhDNase less than the 1 mM $CaCl_2$formulation. Therefore, the physical stability of the 0/1 mM $CaCl_2$ formulation lies somewhat in between the 1 mM $CaCl_2$formulation and the one treated with EDTA. A possible formulation for the portable ultrasonic nebulizer is 40–50 mg/mL rhDNase in 1 mM NaOAc, 30 mM $CaCl_2$, 105 mM NaCl, pH 5.3.

TABLE 4

First Order Rate Constants for Deamidation in rhDNase as Assessed by Tentacle Ion Exchange Chromatography

|  | 1 mg/mL rhDNase 5 mM buffer*, 150 mM NaCl 1 mM $CaCl_2$ | | 50 mg/ml rhDNase 150 mM NaCl 1 mM $CaCl_2$ | |
|---|---|---|---|---|
|  | pH 5 | pH 6 | pH 5 | pH 6 |
| 25° C. | 7 ± 1 × $10^{-4}$ | 1.6 ± 0.1 × $10^{-3}$ | 8.5 ± 0.6 × $10^{-4}$ | 2.1 ± 0.1 × $10^{-3}$ |
| 37° C. | 3.7 ± 0.2 × $10^{-3}$ | 9.96 ± 0.2 × $10^{-3}$ | 4.9 ± 0.2 × $10^{-3}$ | 1.02 ± 0.05 × $10^{-2}$ |

*Acetate, pH 5
Succinate, pH 6

TABLE 5

Visual Inspection of the Supernatants of 50 mg/mL rhDNase in 150 mM NaCl, 1–200 mM $CaCl_2$, pH 5 after Centrifugation and Storage at 37° C.

| Sample * 50 mg/mL rhDNase 150 mM NaCl pH 5 | T = 0, 2, 5 days | Color/Clarity at 37° C. T = 7 days |
|---|---|---|
| 1 mM $CaCl_2$ | co/cl | co/sl opa |
| 10 mM $CaCl_2$ | co/cl | co/cl |
| 20 mM $CaCl_2$ | co/cl | co/cl |
| 50 mM $CaCl_2$ | co/cl | co/cl |
| 100 mM $CaCl_2$ | co/cl | co/cl |
| 200 mM $CaCl_2$ | co/cl | co/cl |

* 50 mg/mL rhDNase in 150 mM NaCl, 1 mM $CaCl_2$, was prepared by Amicon ultrafiltration. The 10–200 mM $CaCl_2$ was incorporated into the formulation by dialysis and the final solutions were acid titrated to pH 5 with HCl. The samples were stored at 37° C. for more than 30 days. The supernatants of these samples were obtained after centrifugation at 13,000 rpm for 10 min at ambient temperature.
Keys:
co = colorless, cl = clear with no particulate, sl opa = slightly opalescent

TABLE 6 pH and Color & Clarity of 50 mg/mL rhDNase in unbuffered $CaCl_2$ isotonic with NaCl. pH 4.7 at 37° C.

| Sample | Day | Color/Clarity | pH |
|---|---|---|---|
| 1 mM $CaCl_2$, 150 mM NaCl | 0 | 0/0 | 5.06 |
|  | 28 | 0/3 | 5.28 |
| 10 mM $CaCl_2$, 135 mM NaCl | 0 | 0/0 | 4.94 |
|  | 28 | 0/3 | 5.02 |
| 25 mM $CaCl_2$, 112 mM NaCl | 0 | 0/0 | 5.31 |
|  | 28 | 0/0 | 5.36 |

TABLE 6-continued pH and Color & Clarity of 50 mg/mL rhDNase in unbuffered CaCl$_2$ isotonic with NaCl. pH 4.7 at 37° C.

| Sample | Day | Color/Clarity | pH |
|---|---|---|---|
| 50 mM CaCl$_2$, 75 mM NaCl | 0 | 0/0 | 5.01 |
| | 28 | 0/0 | 5.05 |

Keys:
Color: 0 = colorless
Clarity: 0 = clear 1 = opalescent 2 = slightly cloudy 3 = cloudy

TABLE 7 pH, Color & Clarity of 50 mg/ml rhDNase in 0.25–1 mM Acetate buffer, 1–50 mM CaCl$_2$, isotonic with NaCl, pH 5 at 37° C.

| Sample | Day | Color/Clarity | pH |
|---|---|---|---|
| 0.25 mM NaOAc, 1 mM CaCl$_2$, 150 mM NaCl | 0 | 0/0 | 5.55 |
| | 28 | 0/3 | 5.63 |
| 0.25 mM NaOAc, 10 mM CaCl$_2$, 135 mM NaCl | 0 | 0/0 | 5.54 |
| | 28 | 0/0 | 5.59 |
| 0.25 mM NaOAc, 25 mM CaCl$_2$, 112 mM NaCl | 0 | 0/0 | 5.37 |
| | 28 | 0/0 | 5.43 |
| 0.25 mM NaOAc, 50 mM CaCl$_2$, 75 mM NaCl | 0 | 0/0 | 5.23 |
| | 28 | 0/0 | 5.28 |
| 0.5 mM NaOAc, 1 mM CaCl$_2$, 150 mM NaCl | 0 | 0/0 | 5.25 |
| | 28 | 0/3 | 5.41 |
| 0.5 mM NaOAc, 10 mM CaCl$_2$, 135 mM NaCl | 0 | 0/0 | 5.24 |
| | 28 | 0/1 | 5.28 |
| 0.5 mM NaOAc, 25 mM CaCl$_2$, 112 mM NaCl | 0 | 0/0 | 5.37 |
| | 28 | 0/0 | 5.43 |
| 0.5 mM NaOAc, 50 mM CaCl$_2$, 75 mM NaCl | 0 | 0/0 | 5.31 |
| | 28 | 0/0 | 5.36 |
| 1 mM NaOAc, 1 mM CaCl$_2$, 150 mM NaCl | 0 | 0/0 | 5.14 |
| | 28 | 0/3 | 5.34 |
| 1 mM NaOAc, 10 mM CaCl$_2$, 135 mM NaCl | 0 | 0/0 | 5.18 |
| | 28 | 0/1 | 5.23 |
| 1 mM NaOAc, 25 mM CaCl$_2$, 112 mM NaCl | 0 | 0/0 | 5.25 |
| | 28 | 0/0 | 5.30 |
| 1 mM NaOAc, 50 mM CaCl$_2$, 75 mM NaCl | 0 | 0/0 | 5.10 |
| | 28 | 0/0 | 5.14 |

Keys:
Color: 0 = colorless
Clarity: 0 = clear 1 = opalescent 2 = slightly cloudy 3 = cloudy

TABLE 8

Effect of Ca$^{++}$ and Ionic Strength on Precipitation of 50 mg/mL rhDNase at pH 5, 37° C.

| Sample | Ionic Strength | Color/Clarity T = 0 | T = 1,3 days |
|---|---|---|---|
| By Acid titration to pH 5: | | | |
| 150 mM NaCl, 1 mM CaCl$_2$ | 0.153M | co/cl | co/PO |
| 150 mM NaCl, 1 M CaCl$_2$ | 3.15 M | co/cl | co/cl |
| 3.15 M NaCl, 1 mM CaCl$_2$ | 3.15 M | co/cl | co/cl |
| By dialysis into pH 5 Acetate buffer: | | | |
| 1 mM NaOAc, 150 mM NaCl, 1 mM CaCl$_2$ | 0.154M | co/cl | co/PO |
| 1 mM NaOAc, 75 mM NaCl, 50 mM CaCl$_2$ | 0.226M | co/cl | co/cl |
| 1 mM NaOAc, 222 mM NaCl, 1 mM CaCl$_2$ | 0.226M | co/co | co/PO |

Keys:
0 = colorless cl = clear PO = precipitates observed

TABLE 9

Comparison of Ca$^{++}$: Determination of rhDNase by LC and AA

| | Ca$^{++}$ (mM) | | mole Ca/mole rhDNase | |
|---|---|---|---|---|
| Sample | LC | AA | Theoretical | Experimental (AA) |
| 1 mg/mL (0.0303 mole rhDNase) 150 mM NaCl, 1 mM CaCl$_2$ | — | 1.18 1.1 | 33.00 | 38.94 36.30 |
| 4.7 mg/mL (0.142 mole rhDNase) 150 mM NaCl, 1 mM CaCl$_2$ | — | 1.60 1.63 | 7.04 | 11.27 11.48 |
| 5.9 mg/mL (0.179 mole rhDNase) 150 mM NaCl, 1 mM CaCl$_2$ | — | 1.65 1.80 | 5.59 | 9.22 10.06 |
| 10 mg/mL (0.303 mole rhDNase) 150 mM NaCl, 1 mM CaCl$_2$ | — | 2.28 2.33* 2.33 2.34* | 3.30 7.76* | 7.52 7.72* 7.39 |
| 40.83 mg/mL (1.24 mole rhDNase) 150 mM NaCl | 1.45 1.48 | 1.73 1.65 | 0 | 1.40 1.33 |
| 41.71 mg/mL (1.26 mole rhDNase) 150 mM NaCl, 0/1 mM CaCl$_2$ | 3.95 | 3.90 3.83 | 0.79 | 3.09 3.04 |
| 45.96 mg/mL (1.39 rhDNase) 150 mM NaCl, 1 mM CaCl$_2$ | 5.43 5.60 | 6.03 5.80 | 0.72 | 4.53 4.17 |
| 48.77 mg/mL (1.48 mole rhDNase) 150 mM NaCl, 1 mM CaCl$_2$ | 6.23 | 6.08 6.23 | 0.68 | 4.11 4.21 |
| 43.15 mg/mL (1.31 mole rhDNase) 150 mM NaCl, 10 mM CaCl$_2$ | 20.00 16.08 | 17.00 16.13 | 7.63 | 12.78 12.31 |
| 43.81 mg/mL (1.33 mole rhDNase) 150 mM NaCl, 20 mM CaCl$_2$ | 35.00 25.50 | 27.38 26.13 | 15.04 | 20.59 19.62 |
| 45.20 mg/mL (1.37 mole rhDNase) 150 mM NaCl, 50 mM CaCl$_2$ | 70.00 56.70 | 57.25 55.00 | 36.50 | 41.79 40.15 |
| 51.47 mg/mL (1.56 mole rhDNase) 150 mM NaCl, 100 mM CaCl$_2$ | 114.15 | 111.88 106.25 | 64.10 | 71.72 68.11 |
| 53.50 mg/mL (1.62 mole rhDNase) 150 mM NaCl, 200 mM CaCl$_2$ | 211.75 | 205.00 | 123.46 | 126.54 |

[a]*EDTA treated
[b]EDTA treated and 1 mM CaCl$_2$ is dialyzed back into the formulation
*Analysis by Balco Bay Area Laboratory CoOperative, Burlingame, CA.

Concluding Remarks

The foregoing description details specific methods which can be employed to practice the present invention. Having detailed specific methods used to prepare and characterize and therapeutically administer the formulation of DNase hereof, and further disclosure as to specific model systems pertaining thereto, those skilled in the art will well enough know how to devise alternative reliable methods for arriving at the same information in using the fruits of the present invention. Thus, however detailed the foregoing may appear in text, it should not be construed as limiting the overall scope thereof, rather the ambit of the present invention is to be determined solely by the lawful construction of the appended claims.

What is claimed is:

1. A process for minimizing the aggregation of DNase at elevated temperatures comprising:

introducing a DNase aggregation-inhibiting amount of calcium cation to a solution comprising DNase, wherein the temperature of said solution is subsequently elevated to above 37° C. and aggregation of DNase at said elevated temperature is minimized.

2. The process according to claim 1 wherein said elevation of temperature results from spray-drying for collection as a respirable DNase-containing powder that is therapeutically effective when administered into the lung of an individual.

3. A process according to claim 1, wherein the temperature of said solution is elevated above about 60° C.

4. A process according to claim 1, wherein said calcium cation is supplied by calcium chloride, calcium oxide or calcium carbonate.

5. A process according to claim 1, wherein said calcium cation is present in an amount from 1 mM to 1 M in said solution.

6. A process according to claim 5, wherein said calcium cation is supplied by calcium chloride in an amount from 10 mM to 100 mM in said solution.

* * * * *